（12） United States Patent
Kadykowski

(10) Patent No.: US 10,398,527 B2
(45) Date of Patent: Sep. 3, 2019

(54) SURGICAL TISSUE MARKING DEVICE WITH DRYER

(71) Applicant: TERUMO CARDIOVASCULAR SYSTEMS CORPORATION, Ann Arbor, MI (US)

(72) Inventor: Randal James Kadykowski, South Lyon, MI (US)

(73) Assignee: Terumo Cardiovascular Systems Corporation, Ann Arbor, MI (US)

( * ) Notice: Subject to any disclaimer, the term of this patent is extended or adjusted under 35 U.S.C. 154(b) by 104 days.

(21) Appl. No.: 15/668,902

(22) Filed: Aug. 4, 2017

(65) Prior Publication Data
US 2018/0042694 A1 Feb. 15, 2018

Related U.S. Application Data

(60) Provisional application No. 62/373,563, filed on Aug. 11, 2016.

(51) Int. Cl.
| | |
|---|---|
| *A61B 90/00* | (2016.01) |
| *A61B 18/02* | (2006.01) |
| *A61M 37/00* | (2006.01) |
| *B43K 29/00* | (2006.01) |
| *B43K 8/00* | (2006.01) |
| *A61B 18/04* | (2006.01) |
| *B43K 27/08* | (2006.01) |
| *B43K 8/02* | (2006.01) |
| *A01K 11/00* | (2006.01) |
| *A61B 18/20* | (2006.01) |

(52) U.S. Cl.
CPC ............ *A61B 90/39* (2016.02); *A01K 11/005* (2013.01); *A61B 18/02* (2013.01); *A61B 18/04* (2013.01); *A61M 37/0076* (2013.01); *B43K 8/006* (2013.01); *B43K 8/02* (2013.01); *B43K 27/08* (2013.01); *B43K 29/00* (2013.01); *A61B 18/20* (2013.01); *A61B 2090/395* (2016.02); *A61B 2090/3937* (2016.02); *A61M 37/0084* (2013.01)

(58) Field of Classification Search
CPC combination set(s) only.
See application file for complete search history.

(56) References Cited

U.S. PATENT DOCUMENTS

| | | | |
|---|---|---|---|
| 5,137,038 A * | 8/1992 | Kingsford | ............ A45D 40/265 132/218 |
| 5,226,419 A | 7/1993 | Hanrahan et al. | |
| 5,496,304 A | 3/1996 | Chasan | |
| 6,197,034 B1 | 3/2001 | Gvozdic et al. | |

(Continued)

FOREIGN PATENT DOCUMENTS

EP 0092359 A2 10/1983

*Primary Examiner* — David J Walczak
(74) *Attorney, Agent, or Firm* — Darryl Newell; MacMillan, Sobanski & Todd, LLC

(57) ABSTRACT

A marking/drying tool applies ink to biological tissue using a single handheld device. A cylindrical body retains a felt tip movable between a retracted position within the body and an extended position outside the body for marking the tissue. A gas source has a manual valve to selectably dispensing a drying gas onto the tissue. In a preferred embodiment, an interlock prevents dispensing of drying gas when the tip is in the extended position and prevents the tip moving to the extended position when the manual valve is dispensing the drying gas.

7 Claims, 4 Drawing Sheets

(56) References Cited

U.S. PATENT DOCUMENTS

| | | | |
|---|---|---|---|
| 7,090,420 B2* | 8/2006 | De La Poterie | A45D 2/48 |
| | | | 132/216 |
| 8,123,672 B2 | 2/2012 | Viitala et al. | |
| 8,327,859 B2* | 12/2012 | Pastore | A45D 40/18 |
| | | | 132/218 |
| 9,173,718 B2 | 11/2015 | Kadykowski | |
| 9,668,563 B2* | 6/2017 | Shorland | A45D 34/041 |
| 2003/0090011 A1 | 5/2003 | Bolton | |
| 2006/0079910 A1 | 4/2006 | Tartaglia | |
| 2013/0213424 A1* | 8/2013 | Kim | A45D 29/11 |
| | | | 132/73.6 |

* cited by examiner

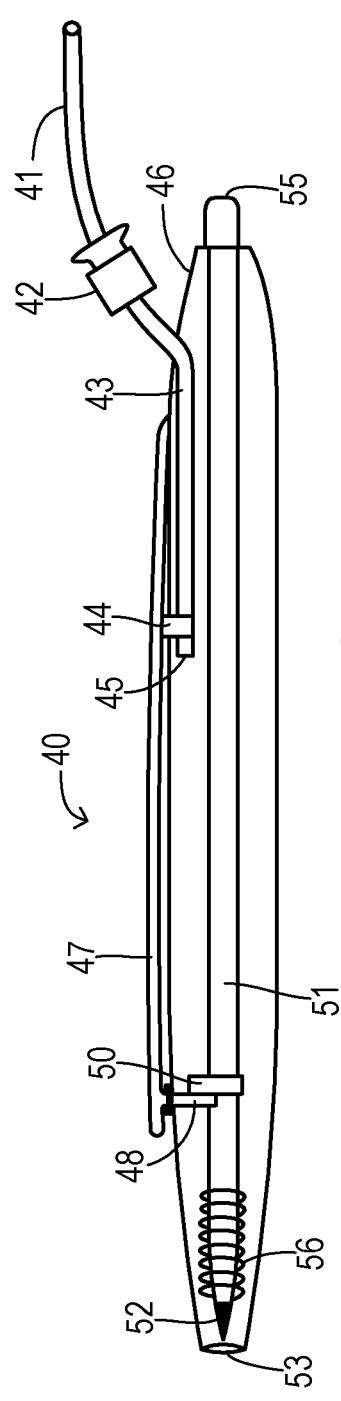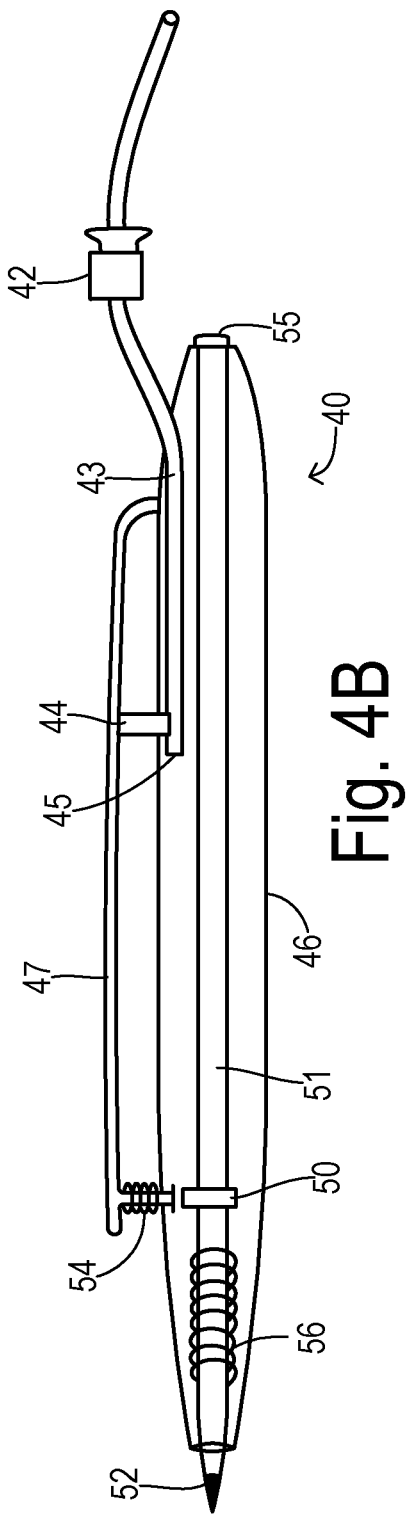
Fig. 4A
Fig. 4B

SURGICAL TISSUE MARKING DEVICE WITH DRYER

CROSS REFERENCE TO RELATED APPLICATIONS

This application claims priority to provisional application Ser. No. 62/373,563, filed on Aug. 11, 2016, which is incorporated herein by reference in its entirety.

STATEMENT REGARDING FEDERALLY SPONSORED RESEARCH

Not Applicable.

BACKGROUND OF THE INVENTION

The present invention relates in general to tools for marking biological tissue during surgical procedures, and, more specifically, to improved accuracy and integrity of tissue marking by drying of the biological tissue.

In preparation for cutting, suturing, or other surgical steps, a surgeon may first identify and mark locations on tissue to properly orient and locate targeted tissue. For example, in coronary artery bypass grafting (CABG), a blood vessel is "harvested" (i.e., removed) from its natural location in a patient's body and reattached elsewhere to create a blood flow around a blockage. After a vessel is removed from the patient's body, it must be prepared for use as a bypass graft. Preparation includes ligating (i.e., closing off) each branch stub, injecting a solution into the vein under pressure to test for leaks, and otherwise inspecting the condition of the blood vessel. After preparation, the vessel can be surgically anastomosed to create the bypass.

It has become common for vessel preparation to include application of a longitudinal guide line along the outer wall of the graft comprised of a methylene blue dye. The line is intended to help in laying out the graft by showing if the graft becomes twisted, which could cause kinking and poor blood flow through the bypass. To apply the guide line, a surgeon or physician's assistant has manually marked the vessel using a felt tip pen filled with the methylene blue dye. The vessel is kept moist with heparinized saline to preserve it while outside the body. The moisture, however, can cause the dye to "run" or diffuse so that the lines blur. This makes it difficult to achieve the pin-point accuracy desired for many procedures.

Other examples of wet tissue marking include 1) marking the internal surface of a live human aortic valve (which are wet from saline and blood) during repair of the valve to indicate suture positions, 2) internally marking cadavers and living animal tissues for various procedures and for marking dissected specimens, and 3) marking the outer surface of wet human eyes.

In addition to marking with a dye such as methylene blue, other means of marking tissue such as laser scoring, tattooing, heat burning, and cold burning can also be adversely affected by moisture on the tissue surface to be marked.

SUMMARY OF THE INVENTION

The present invention provides tools capable of reducing moisture on biological tissue to enhance the ability to accurately mark desired lines or patterns on the tissue using ink or dye. The devices improve surgical outcomes through faster and clearer tissue marking on wet tissue compared to conventional dye marker pens which may tend to produce blurred lines on wet tissue.

The invention provides a marking device including a "blow-dry feature" to reduce moisture using a flow of drying gas (e.g., pressurized $CO_2$). Drying of the wet tissue may be short lived since surrounding moisture may quickly spread back to the dried area. Therefore, the marker and dryer nozzle are contained within a common housing which allows the user to quickly switch between the drying and marking functions. Preferably, one or both of the marker tip and/or gas nozzle is retractable or otherwise shielded from the other to avoid an airbrush effect wherein the dye may be inadvertently dispersed onto the tissue.

According to one aspect of the invention, a wet tissue marking system comprises a marking tip, a gas nozzle, and a holding body. The holding body contains the marking tip and gas nozzle whereby a user dries a wet tissue surface by metering a drying gas onto the surface and reconfigures the system to mark the surface with the marking tip.

BRIEF DESCRIPTION OF THE DRAWINGS

FIGS. 4A and 4B are diagrammatic views of another embodiment of a combined marking and drying tool with an interlock mechanism to prevent emission of drying gas when a marker is extended.

DETAILED DESCRIPTION OF PREFERRED EMBODIMENTS

Figure 1:
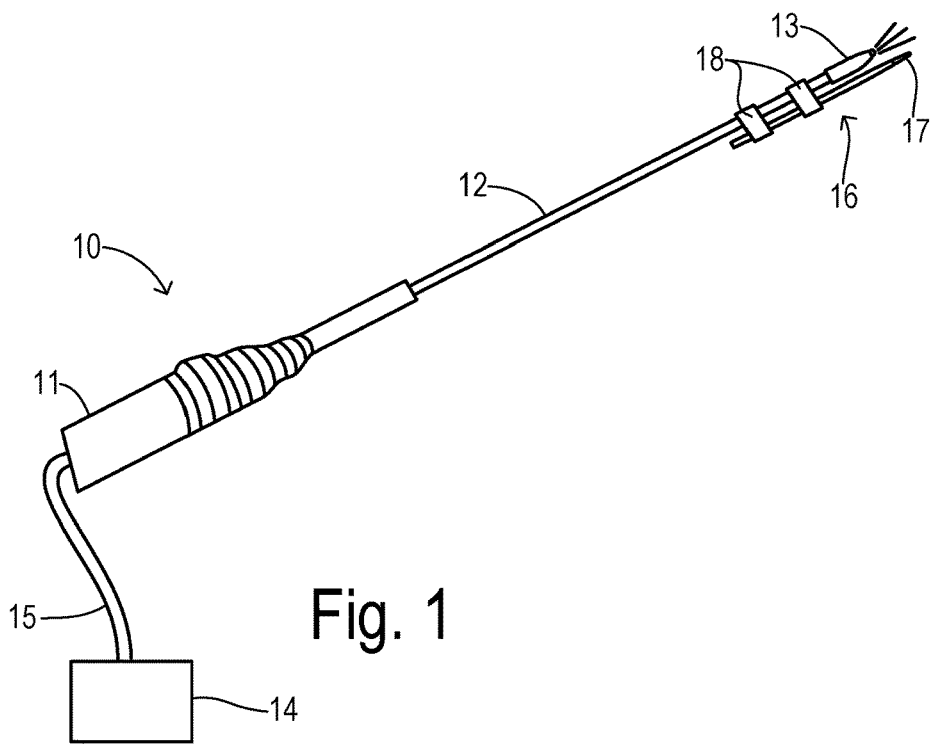
FIG. 1 is a plan view showing one embodiment of a combination tool for drying and marking biological tissue.

FIG. 1 shows a combination tool 10 providing blow dryer and marker functions. A handle 11 supports a hollow rod 12 having a nozzle 13 at its distal end. A drying gas such as $CO_2$ is supplied to nozzle 13 through rod 12 and handle 11 from an external source 14 connected by a supply tube 15. The $CO_2$ gas is commonly available in a surgical facility via a standard luer fitting or a gas cartridge or cylinder, for example. A wet tissue area to be marked can be temporarily dried by metering the gas through nozzle 13 toward the area. A marker device 16 with a tip 17 is mounted to rod 12 adjacent nozzle 13 by straps 18. Tip 17 is preferably comprised of a fine tip surgical marker for methylene dye. Alternatively, a laser emitter for ablating tissue to create a mark, a needle or set of needles for creating a tattoo, a heating element for burning a mark, or a cold burn element for burning a mark can be used.

Figure 2:
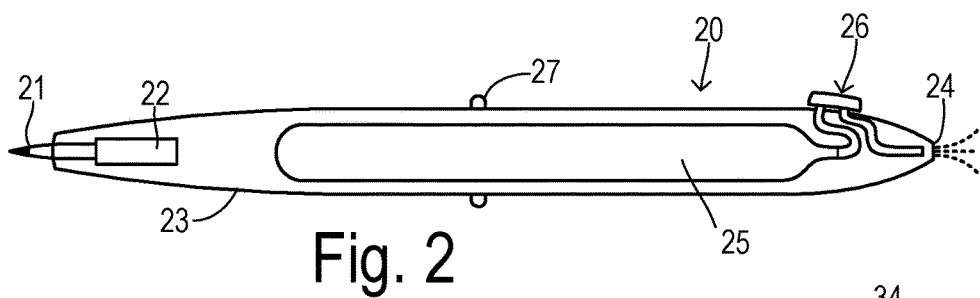
FIG. 2 is a plan view of another embodiment including a double-ended marking and drying tool.

FIG. 2 shows a self-contained device 20 having an overall cylindrical shape similar to a writing pen. At one end, a felt tip 21 delivers dye or ink from a reservoir 22 within a cylindrical body or tube 23. A $CO_2$ nozzle 24 at the other end selectably delivers a gas flow from a $CO_2$ cartridge 25 mounted within body 23 via a valve 26 that is manually controlled by a push button on the side of cylindrical body 23. An annular ridge 27 is provided at the longitudinal center of body 23 to assist with gripping and reversing the orientation of the body (i.e., flipping) after the desired area has been dried so that the tissue can be marked as desired.

Figure 3A:
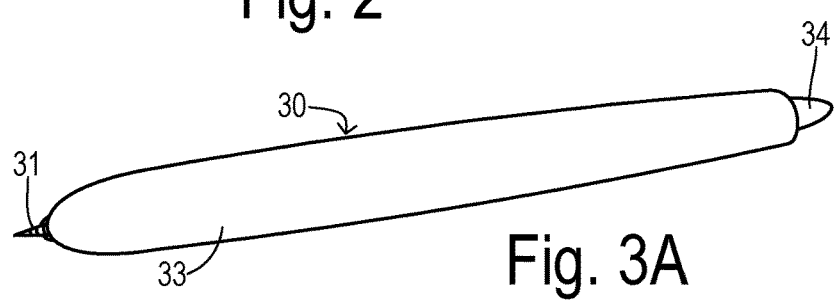
FIGS. 3A and 3B are plans views of another embodiment having a retractable marker and an internal source of drying gas, with the marker extended and retracted, respectively.
Figure 3B:
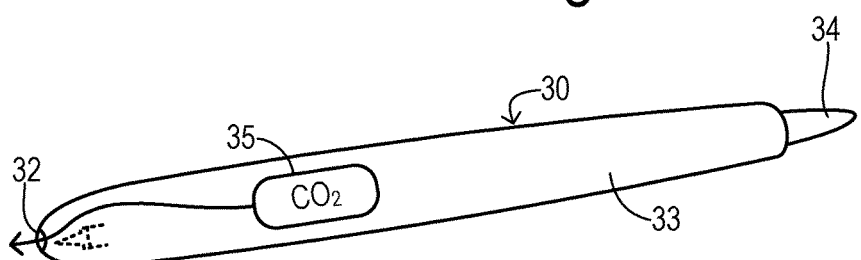

FIGS. 3A and 3B show an alternative embodiment wherein reversing of a device 30 is not required (i.e., the marker and dryer nozzle deploy from the same working end of the cylindrical body). One or both of a marking tip 31 and gas nozzle 32 are retractable so that each of the drying and marking functions can be performed without interference by the other function (e.g., no air brushing of the dye). In FIG. 3A, marking tip 31 is extended from a cylindrical body 33. A retractable pen-type structure with a rotating cam body (not shown) activated by a push button 34 at the opposite end of cylindrical body 33 is used for selectably extending tip 31 out from a nozzle opening at the end of body 33. In FIG. 3B, tip 31 is retracted. When tip 31 clears the opening, a gas nozzle may be extended in order to dispense gas from a cartridge 35. Alternatively, it is not necessary to provide an extendible nozzle as long as marking tip 31 retracts to a position behind nozzle opening 32 so that the gas can escape.

FIGS. 4A and 4B show another embodiment of a retractable dryer/marker tool 40 in greater detail. A gas line 41 from an external supply connects to an internal line 43 via a luer fitting 42. Internal line 43 connects to a valve 44 which selectably releases the gas to an internal opening or nozzle 45. Valve 44 is opened and closed via a first plunger arm extending into a tubular body 46 from a gas lever 47 that extends longitudinally along the side of tube 46. A proximal end of lever 47 attaches to tube 46. At the distal end of gas lever 47, a second plunger arm 48 interfaces with a stop block 50 carried by an extendable/retractable marker shaft 51. A marker tip 52 is disposed at the distal end of shaft 51. When marker tip 52 is retracted within tubular body 46 as shown in FIG. 4A, second plunger arm 48 is not deflected by stop block 50, which allows the first plunger arm to open gas valve 44, thereby metering the drying gas through tubular body 46 and out from an opening 53 in the distal end to dry the target tissue. The plunger arms and stop block form an interlock that ensures that tip 52 must be retracted in order for valve 44 to be activated. A spring 54 installed over plunger arm 48 urges lever 47 away from tube 46 so that valve 44 is normally turned off. In order to be able to lever 47 to move toward tube 46, shaft 51/tip 52 must be retracted so that stop block 50 is not preventing incursion of plunger arm 48.

The retraction/extension of shaft 51/tip 52 is controlled using a push button 55 at the proximal end. In a preferred embodiment, a retractable (i.e., click-type) pen mechanism which includes a spring 56 is used to selectably extend or retract marking tip 52 through opening 53. Thus, stop block 50 is placed into an interfering condition with second plunger arm 48 except when tip 52 is retracted. After being configured to dispense the drying gas by holding down gas lever 47, second plunger arm penetrates to the position shown in FIG. 4A which prevent extension of shaft 51 because of interference of stop block 50 and plunger arm 48. When marker shaft 51 is extended, gas lever 47 is deflected radially outward so that the first plunger arm moves away from gas valve 44, and gas valve 44 closes to prevent gas from being emitted at the distal end.

Figure 5:
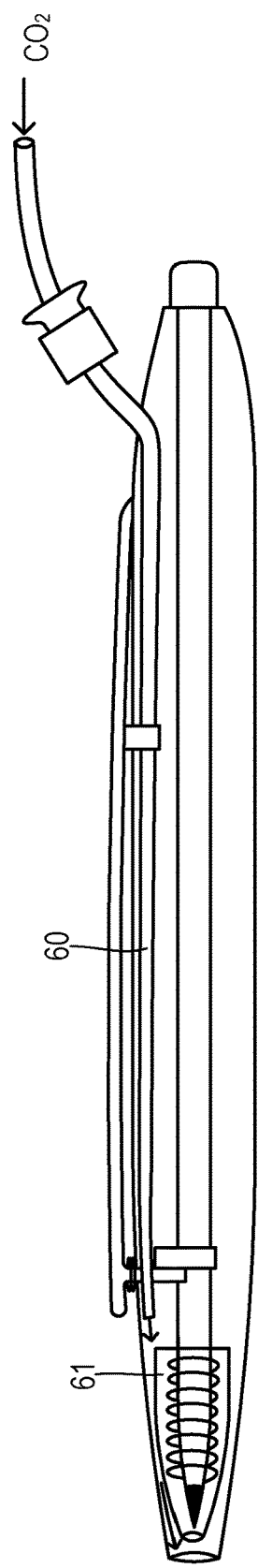
FIG. 5 is a diagrammatic view of a modified embodiment.

As shown in FIG. 5, it may be preferable to provide an extend internal gas line 60 so that free flow of the drying gas initiates beyond a retracted position of the marker tip so that the drying gas is not blown over the marker. Alternatively, an internal shield wall or tube 61 can be placed around the marker tip's retracted position to separate the tip from the gas flow.

Figure 6:
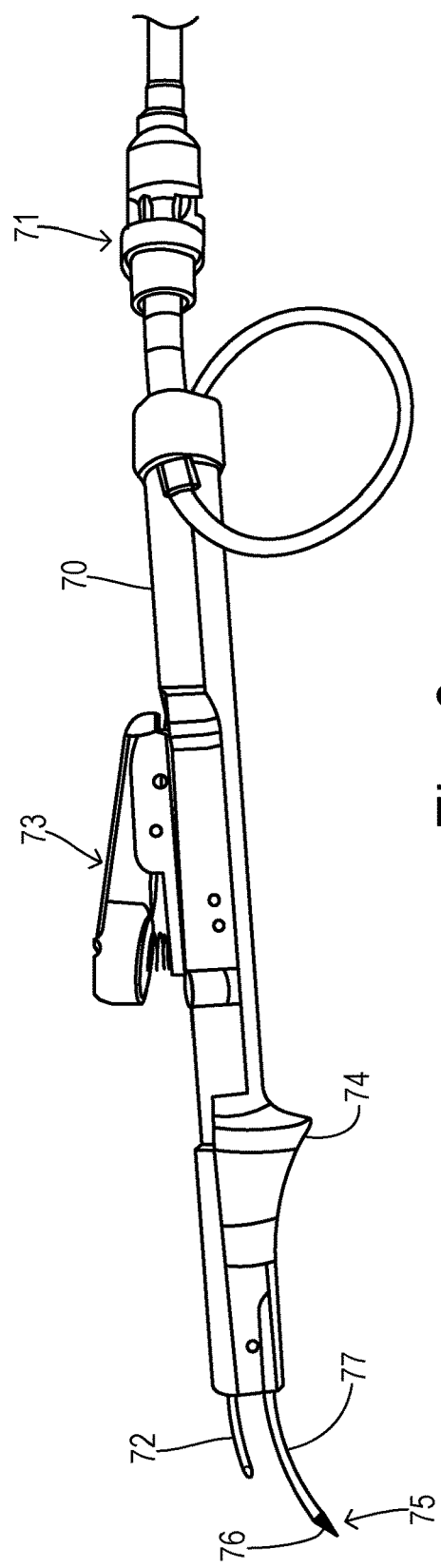
FIG. 6 is a side view of another embodiment wherein a marking tip is carried by a malleable shaft.

FIG. 6 shows another embodiment wherein a tool body 70 is fitted with a gas supply luer connection 71 at the proximal end and a gas ejection tube 72 at the distal end. A thumb activated gas valve 73 is placed behind a finger grip 74 for convenient manipulation of body 70. A marking portion 75 includes a dye marker felt tip 76 attached to a distal end of a malleable support shaft 77 that extends from body 70. A user can manually bend shaft 77 in order to configure the placement of tip 76 for better visualization in tight areas such as internal aortic valve sections.

In the embodiment of FIG. 6, tip 76 is not retractable. Alternatively, a felt tip holder tube and a linkage from a sliding control button could be provided. In either case, shaft 77 may be pre-bent so that where felt tip 76 is placed for tissue contact, it is held at an angle to main body 70. This affords the user better visibility. Typically, straight markers would obstruct the place that you are trying to mark. In the case of a felt tip, when it retracts into a bent tube it can return to being straight once it is back inside the tube holder.

What is claimed is:

1. A wet tissue marking system for marking wet biological tissue to guide a surgery, comprising:
    a marking tip;
    a gas nozzle;
    a holding body containing the marking tip and gas nozzle, wherein the marking tip and gas nozzle remain contained by and extend from the holding body, whereby a user dries a wet tissue surface of the wet biological tissue by metering a drying gas onto the surface and reconfigures the system to mark the dried surface with the marking tip, wherein at least one of the marking tip and the gas nozzle is retractable into the holding body.

2. The system of claim 1 wherein the marking tip is selected from the group comprising a methylene blue felt tip, a laser, a tattoo unit, a heating element, or a cold burning element.

3. The system of claim 1 wherein the marking tip is shielded from the drying gas ejected from the gas nozzle.

4. The system of claim 1 wherein the holding body includes a malleable support shaft carrying the marking tip.

5. A marking/drying tool for applying ink to biological tissue comprising:
    a cylindrical body,
    a felt tip movable between a retracted position within the body and an extended position outside the body for marking the tissue;
    a gas source with a manual valve to selectably dispensing a drying gas onto the tissue; and
    an interlock for preventing dispensing of drying gas when the tip is in the extended position.

6. The tool of claim 5 wherein the interlock prevents the tip moving to the extended position when the manual valve is dispensing the drying gas.

7. The tool of claim 6 further comprising a malleable support shaft for the felt tip.

* * * * *